(12) United States Patent
Long et al.

(10) Patent No.: US 9,394,503 B2
(45) Date of Patent: Jul. 19, 2016

(54) SEPARATION PROCESS OF OIL AND SUGARS FROM BIOMASS

(71) Applicant: The Board of Trustees of the University of Illinois, Urbana, IL (US)

(72) Inventors: Stephen P Long, Champaign, IL (US); Vijay Singh, Savoy, IL (US); Haibo Huang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 4 days.

(21) Appl. No.: 14/514,206

(22) Filed: Oct. 14, 2014

(65) Prior Publication Data

US 2015/0105546 A1 Apr. 16, 2015

Related U.S. Application Data

(60) Provisional application No. 61/891,211, filed on Oct. 15, 2013.

(51) Int. Cl.

| | |
|---|---|
| *C08B 37/00* | (2006.01) |
| *C11B 3/00* | (2006.01) |
| *C11B 3/16* | (2006.01) |
| *A61K 36/899* | (2006.01) |
| *C11B 1/10* | (2006.01) |
| *C07H 3/04* | (2006.01) |
| *C11B 1/06* | (2006.01) |
| *B02C 23/08* | (2006.01) |
| *C07H 1/08* | (2006.01) |
| *C11B 1/04* | (2006.01) |

(52) U.S. Cl.
CPC . *C11B 1/10* (2013.01); *B02C 23/08* (2013.01); *C07H 1/08* (2013.01); *C07H 3/04* (2013.01); *C11B 1/04* (2013.01); *C11B 1/06* (2013.01); *C11B 3/006* (2013.01); *C11B 3/008* (2013.01); *C11B 3/16* (2013.01)

(58) Field of Classification Search
CPC ............. A61K 36/899; A61K 2300/00; C08B 37/0087
USPC .................................................. 536/128, 124
See application file for complete search history.

(56) References Cited

U.S. PATENT DOCUMENTS

| | | | |
|---|---|---|---|
| 3,418,311 A | * | 12/1968 | Sakai .................. A61K 36/899 536/123 |
| 4,057,437 A | | 11/1977 | Kracklauer |
| 4,376,409 A | | 3/1983 | Belk |
| 6,068,869 A | | 5/2000 | Ginslov |
| 6,166,231 A | | 12/2000 | Hoeksema |
| 6,387,186 B1 | | 5/2002 | Reisig et al. |
| 6,406,548 B1 | | 6/2002 | Donovan et al. |
| 6,433,146 B1 | | 8/2002 | Cheryan |
| 7,148,366 B2 | | 12/2006 | Cheryan |
| 7,601,858 B2 | | 10/2009 | Cantrell et al. |
| 7,868,195 B2 | | 1/2011 | Fleischer et al. |
| 2010/0331580 A1 | | 12/2010 | Ridgley |
| 2013/0164798 A1 | * | 6/2013 | Vanhercke ................ C10L 1/04 435/134 |

OTHER PUBLICATIONS

Hinkova, Andrea, et al, Potentials of separation membranes in the sugar industry. Separation and Purification Technology, 26.1 (2002): 101-110.

Majoni, Sandra, Tong Wang, and Lawrence A. Johnson. Physical and chemical processes to enhance oil recovery from condensed corn distillers solubles. Journal of the American Oil Chemists Society, 88.3 (2011): 425-434.

Raman, Lakshminarayanan Pattabi, Munir Cheryan, and Nandkishore Rajagopalan. Solvent recovery and partial deacidification of vegetable oils by membrane technology. Lipid, 98.1 (1996): 10-14.

Lamsal, B. P., and Johnson, L. A. Separating oil from aqueous extraction fractions of soybean. Journal of American Oil and Chemists Society, 84 (2007): 785-792.

\* cited by examiner

*Primary Examiner* — Patrick Lewis
*Assistant Examiner* — Everett White
(74) *Attorney, Agent, or Firm* — Dilworth IP, LLC

(57) ABSTRACT

Process for recovery and separation of sugars and oil from plants where the stems and leaves of such plants have substantial levels of both sugars and oils.

20 Claims, 5 Drawing Sheets

SEPARATION PROCESS OF OIL AND SUGARS FROM BIOMASS

STATEMENT REGARDING FEDERALLY SPONSORED RESEARCH OR DEVELOPMENT

This invention was made with government support under contract number DOE DE-AR0000206 awarded by the U.S. Department of Energy/Advanced Research Project Agency—Energy. The government has certain rights in the invention.

FIELD OF THE INVENTION

The invention relates to separation processes. More particularly, the invention relates to separation processes for recovering and separating oil and sugars from a biomass.

BACKGROUND OF THE INVENTION

Methods for separating oil and protein from corn are known. For example, U.S. Pat. No. 7,148,366 B2 discloses methods for separating oil and protein from corn and corn products by membrane filtration and solvent extraction. In the '366 patent, an ethanol solution is mixed with dry grind corn to form an extraction solution including ethanol solution, oil and corn solids. The extraction solution is separated into corn solids and a filtrate, with the filtrate including the ethanol solution and oil. The filtrate is membrane-filtered to restrain an oil concentrate from the filtrate and pass a permeate of the ethanol solution.

Further, the separation of sugars from stems and roots, and oil from seeds have been proposed and disclosed. These systems include separating oil from oilseeds and other materials by centrifugation (U.S. Pat. Nos. 7,608,729 B2, 7,601,858 B2), solvent extraction (U.S. Pat. Nos. 7,868,195 B2, 6,166,231) and membrane separation (U.S. Pat. Nos. 6,433,146 B1, 7,148,366 B2). Also, vacuum filtration and centrifugation methods (U.S. Pat. No. 6,387,186) have been disclosed to separate raw sugar solution (juice) from sugar plants, such as sugarcane and sugar beets.

All grasses accumulate sucrose or other non-structural carbohydrates in the stem prior to the initiation of flowering. Their large diameter stems serve as storage organs and are easily pressed commercially to release their liquid contents. Recently, particular genetic and breeding approaches have been made to divert carbon flux from sucrose to oil synthesis and storage in those plants. Unlike traditional plants, the modified plants accumulate substantial amounts of both oil and sugars in their stems and leaves. However, processing methods for the separation of both sugars and oil from stems and leaves of these modified plants have not been reported. Thus, there is a need for improved separation processes/systems capable of separating both sugars and oil from the stems and leaves of modified plants. The present disclosure now provides such a method

SUMMARY OF THE INVENTION

The subject matter of the present disclosure includes separation processes for recovering oil and sugars from a biomass.

In one embodiment, the present disclosure provides a method of recovering oil and sugars from a plant comprising stems and leaves, wherein the stems and leaves each contain oils and sugars. The method comprises mechanically treating the plant to release liquid comprising oil and sugars from the stems and leaves, thereby forming a mechanically treated mixture comprising the liquid and solid components. The mechanical treatment is selected from at least one of shredding, crushing and pressing. Then, the oil is separated from the liquid to form an oil-rich stream. The oil separation step is selected from centrifugation, membrane filtration, or solvent extraction. Next, the sugars are separated from the liquid, thereby forming a sugar-rich solution. The sugar separation step is selected from centrifugation or membrane filtration.

In an alternative embodiment, the present disclosure further provides a method of recovering oils and sugars from a biomass. The method comprises separating the oil from the biomass, thereby forming an oil-rich stream. The oil separation step is selected from centrifugation, membrane filtration, or solvent extraction. Next, the sugars are separated from the biomass, thereby forming a sugar-rich solution. The sugar separation step is selected from centrifugation or membrane filtration. The oil and sugars were both stored in the stems and leaves of a plant.

In another alternate embodiment, the present disclosure further provides a method of recovering oil and sugars from a plant comprising stems and leaves, wherein the stems and leaves each contain oil and sugars. The method comprises mechanically treating the plant to release liquid comprising oil and sugars from the stems and leaves, thereby forming a mechanically treated mixture comprising the liquid and solid components. The mechanical treatment is selected from at least one of shredding, crushing and pressing. Then, the liquid is separated from the solid component in a liquid-solid separation step selected from centrifugation or filtration, thereby forming a separated liquid stream and a separated solid component stream. Next, the oil is separated from the sugars in the separated liquid stream in a solvent extraction step, thereby forming a raw sugar solution stream and a miscella stream comprising oil and solvent. Finally, the solvent is removed from the miscella stream in an evaporation step, thereby forming an oil-rich stream and a solvent recycle stream, and the solvent stream is returned to the solvent extraction step.

In an alternate embodiment, the present disclosure further provides a method of recovering oil and sugars from a plant comprising stems and leaves, wherein the stems and leaves each contain oil and sugars. The method comprises mechanically treating the plant to release liquid comprising oil and sugars from the stems and leaves, thereby forming a mechanically treated mixture comprising the liquid and solid components. The mechanical treatment is selected from at least one of shredding, crushing and pressing. Then, the liquid is separated from the solid component in a liquid-solid separation step selected from centrifugation or filtration, thereby forming a separated liquid stream and a separated solid component stream. Next, the oil is separated from the sugars in the separated liquid stream in a membrane filtration step, thereby forming a raw sugar solution stream and an oil-rich stream comprising oil. The oil in the oil-rich stream is concentrated in an evaporation step, thereby forming a concentrated oil stream.

In still another alternate embodiment, the present disclosure further provides a method of recovering oil and sugars from a plant comprising stems and leaves, wherein the stems and leaves each contain oil and sugars. The method comprises mechanically treating the plant to release liquid comprising oil and sugars from the stems and leaves, thereby forming a mechanically treated mixture comprising the liquid and solid components. The mechanical treatment is selected from at least one of shredding, crushing and pressing. Then, the mechanically treated mixture is extracted in a solvent extraction step, thereby forming a de-oiled material stream comprising sugars and a solid component, and a miscella stream comprising oil and solvent. Next, the solvent is removed from the miscella stream in an evaporation step, thereby forming an oil-rich stream and a solvent recycle stream. The sugars are separated from the solid component in the de-oiled material stream in a membrane filtration step, thereby forming a raw sugar solution and a solid component stream.

In another alternate embodiment, the present disclosure provides a method of recovering oil and sugars from a plant comprising stems and leaves, wherein the stems and leaves each contain oil and sugars. The method comprises mechanically treating the plant to release liquid comprising oil and sugars from the stems and leaves, thereby forming a mechanically treated mixture comprising a juice stream comprising the oil and sugars. The mechanical treatment is selected from at least one of shredding, crushing and pressing. Then the juice stream is fermented in a fermentation step to convert the sugars to ethanol, thereby forming a fermented mixture. Next, the ethanol is evaporated from the fermented mixture in an evaporation step, thereby forming a raw oil stream. The raw oil stream is then extracted in a solvent extraction step to separate oil from the raw oil stream, thereby forming an oil enriched stream.

BRIEF DESCRIPTION OF THE DRAWINGS

The subject matter of the present disclosure will be more fully understood from the following detailed description, taken in connection with the accompanying drawings, in which.

DETAILED DESCRIPTION OF THE INVENTION

The inventive method recovers and separates oil and sugars from plants having substantial amounts of oil and sugars in their stems and leaves by the combined processes of centrifugation, membrane filtration and solvent extraction.

Figure 1:
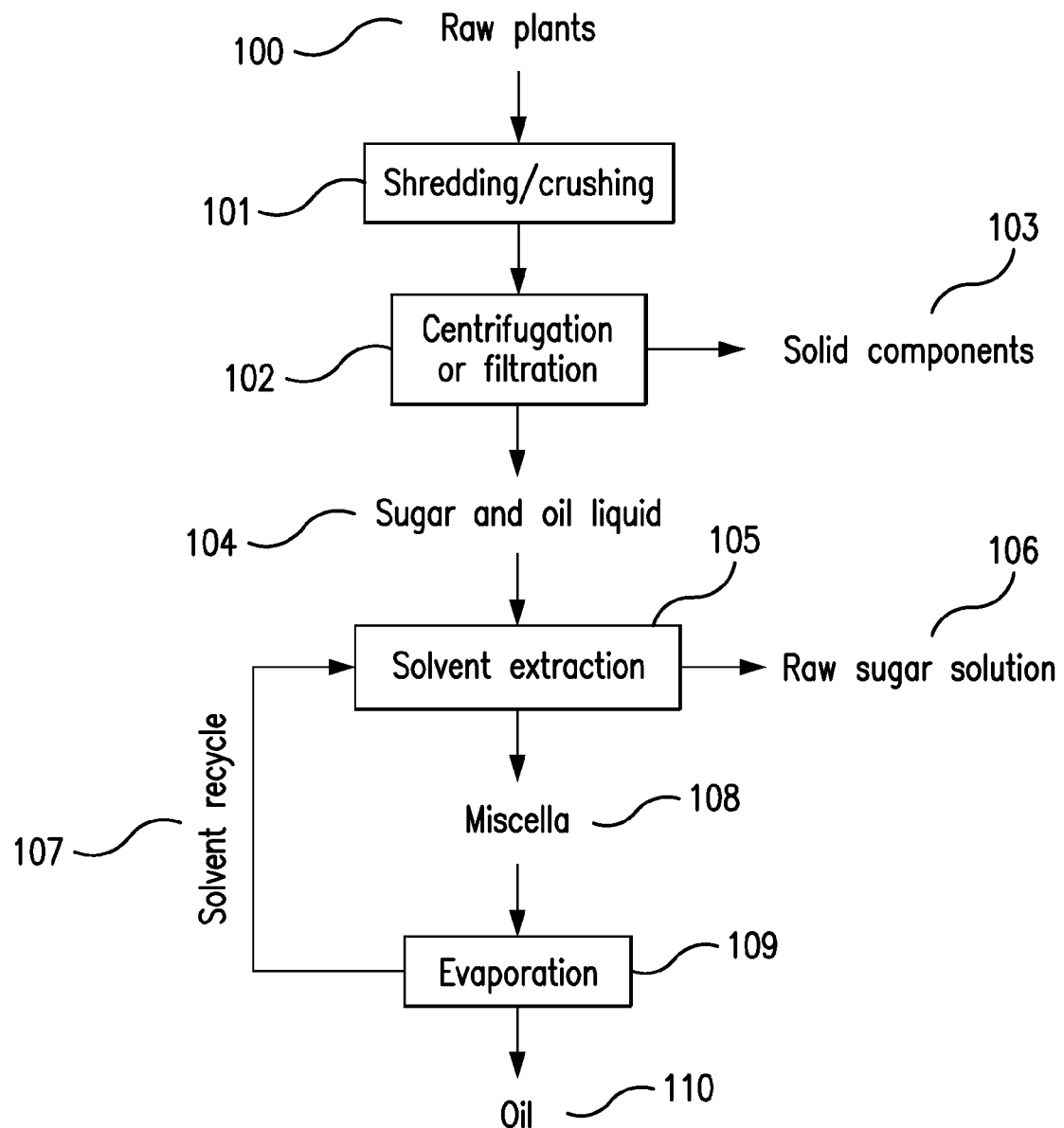
FIG. 1 illustrates a flow diagram of a separation process of oil and sugar by applying centrifugation and solvent extraction.

Referring now to FIG. 1, shown is a flow diagram of a separation process of oil and sugars from raw plants 100 with centrifugation and solvent extraction. For the purpose of this specification, the term "oil," referring to oil contained in the stems and leaves of plants, includes all lipids such as fats, waxes, sterols, monoglycerides, diglycerides, triglycerides, phospholipids and the like. The term "sugar," referring to sugar contained in the stems and leaves of plants, includes sucrose, glucose, fructose, other mono, di, or tri saccharides, or oligomeric sugars. Further, for the purpose of this specification, the term "plant" means a vegetative biomass, i.e., does not contain seeds or fruit. Preferably, the plant is a grass. More preferably, the grass is from the sub-tribe saccharinae. Even more preferably, the grass is selected from sugarcane or sweet sorghum. All grasses accumulate sucrose in their stems prior to flowering. However, the plants utilized in the processes of the present disclosure contain a substantial amount of both oil and sugars in their stems and leaves. This is not the case with conventional vegetative plant biomass where oil is present only in the very low quantities necessary for metabolic functions. For the purpose of this specification, the term "substantial," referring to the concentrations of oil or sugars in the stems or leaves of the plants, means an oil concentration of 0.1 to 25 wt %, preferably, 0.5 to 25 wt % on a dry matter basis, and a sugar concentration of 0.1 to 55 wt %, preferably 1.0 to 55 wt % on a dry matter basis. Preferably, the plants are modified strains developed through targeted genetics and breeding programs so as to divert the carbon flux of the plant from sucrose to oil synthesis/storage. In unmodified strains of plants, the oil contained in the plant stems and leaves is less than 0.1 wt %. Targeted genetics and breeding programs include up-regulation of genes involved in lipid synthesis within vegetative tissues and down regulation of the expression of genes involved in lipid consumption to cause an accumulation of lipids within the vegetative tissue. This may, or may not, include expression of genes producing protein or other coats that may protect lipid globules within these tissues.

In a first step, the raw plants 100 are mechanically treated in a shredding/crushing/pressing step 101 to release liquid containing oil and sugars from the stems and leaves of the plants. The mechanical treatment includes at least one of shredding, crushing and pressing to release the liquid. The shredding equipment used in a shredding step includes any kind of commercially available shredders that can break stems or leaves. The crushing equipment that can be used in a crushing step includes roller mills or juicers. The crushing step can be accompanied by immersion of the shredded plants in water or a solvent such as hexane, and heating the mixture to a temperature of from 100 to 160 DegF, to aid the liquid release from the plant stems and leaves. Equipment used in the pressing step includes roller mills and juicers. In the next step, the mechanically treated mixture is routed to a liquid/solid separation process 102, such as centrifugation or filtration which separates the mechanically treated mixture into a separated liquid stream containing sugar and oil liquid 104 and a separated solid component stream 103 containing insoluble material. Centrifugation equipment can include, for example, centrifuges or hydrocyclones. Centrifuges can include, for example, sedimentation centrifuges having rotor types such as batch, tubular or solid bowl; or filtration centrifuges having screens such as conical or cylindrical screens. Filtration equipment can include pressure filters, vacuum filters or gravity filters. The concentration of solids in the separated liquid stream is 0.1 wt % to 30 wt %. The concentration of solids in the solid component stream is 20 wt % to 60 wt %.

The separated liquid stream containing sugar and oil liquid 104 is then routed to a solvent extraction step 105 where it is contacted with organic solvents, such as hexane to separate the oils from the sugar. The type of extraction equipment that can be used in the extraction step can include mixer-settlers, columns (packed and pulse columns with plates or trays) or centrifugal contactors. The mixer-settlers and centrifugal contactors are discrete-stage units that can be used alone or arranged as a series of stages, with the feed and solvent flow being configured in countercurrent or concurrent operation. The organic solvent is typically contacted with the separated liquid stream for a period of time of about 10 to 120 min at a temperature of 68 to 150 DegF and a pressure of about 101 kPa. Oil is extracted from the separated liquid stream 104 into the organic solvent, and forms an oil/solvent miscella 108. The concentration of oil in the oil/solvent miscella 108 is from 0.1 wt % to more than 50%. Recovery of oil from the separated liquid stream 104 is from 0.5 wt % to 100 wt %, preferably from 5 wt % to 95 wt %. Raffinate from the solvent extraction process 105 is a raw sugar solution 106. The concentration of sugars in the raw sugar solution 106 ranges from 0.1 wt % to 50 wt %. Recovery of sugars in the raw sugar solution from the separated liquid stream 104 is from 0.5 wt % to 100 wt %, preferably from 20 wt % to 96 wt %. The separated miscella 108 is subjected to an evaporation step 109 to remove hexane from the oil so as to form an oil-rich stream 110 and a solvent recycle stream 107. Hexane concentration in the oil-rich stream 110 is from 0.01 wt % to 5 wt %. The organic solvent recovered from this step is recycled to the solvent recycle step 107.

Figure 2:
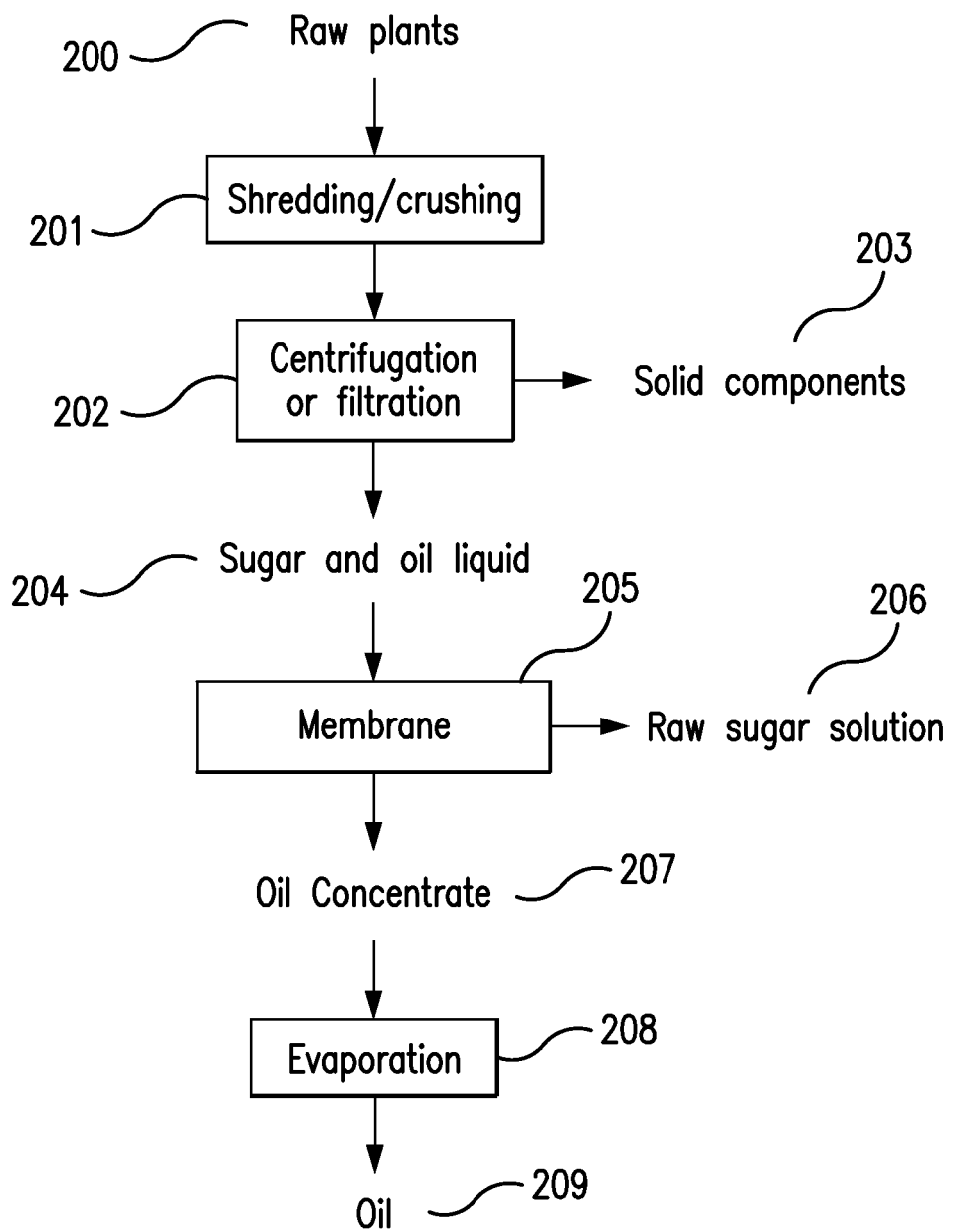
FIG. 2 illustrates a flow diagram of a separation process of oil and sugar by applying centrifugation and membrane filtration

Referring now to FIG. 2, the process of the present disclosure focuses on applying membrane filtration to separate oil from the sugar solution to avoid using a substantial amount of solvent.

In a first step, the raw plants 200 are mechanically treated in a shredding/crushing/pressing step 201 to release liquid containing oils and sugars from the stems and leaves of the plants. The mechanical treatment is as described with regard to mechanical treatment 101 in FIG. 1. In the next step, the mechanically treated mixture is routed to a liquid/solid separation process 202, which is as described for the separation process 102 in FIG. 1. The separated liquid stream containing sugar and oil liquid 204 is then processed in a membrane filtration step 205 to restrain oil (retentate), thereby forming an oil concentrate 207, while allowing sugars to pass through (permeate), thereby forming a raw sugar solution 206. The plant oil has a molecular weight of about 800 to 900 daltons, while sugars (glucose and sucrose) normally have a molecular weight of 180 to 350 daltons. The membrane filter equipment that typically can be used for this step preferably includes: microfiltration units using membranes with a pore size of about 0.03 to 10 microns, and a molecular weight cutoff of greater than 100,000 daltons; ultrafiltration units using membranes with a membrane pore size of about 0.002 to 0.1 microns and a molecular weight cutoff of 10,000 to 100,000 daltons; or nanofiltration units using membranes with a membrane pore size of about 0.001 micron and a molecular weight cutoff of 1,000 to 100,000 daltons. The oil concentrate 207 contains non-oil materials in an amount from 0.1 wt % to 50 wt %. The raw sugar solution 206 contains oil in an amount from 0.1 wt % to 50 wt %. The oil concentrate 207 is subjected to an evaporation step 208 to remove any water and convert the oil concentrate 207 to anhydrate oil 209.

Figure 3:
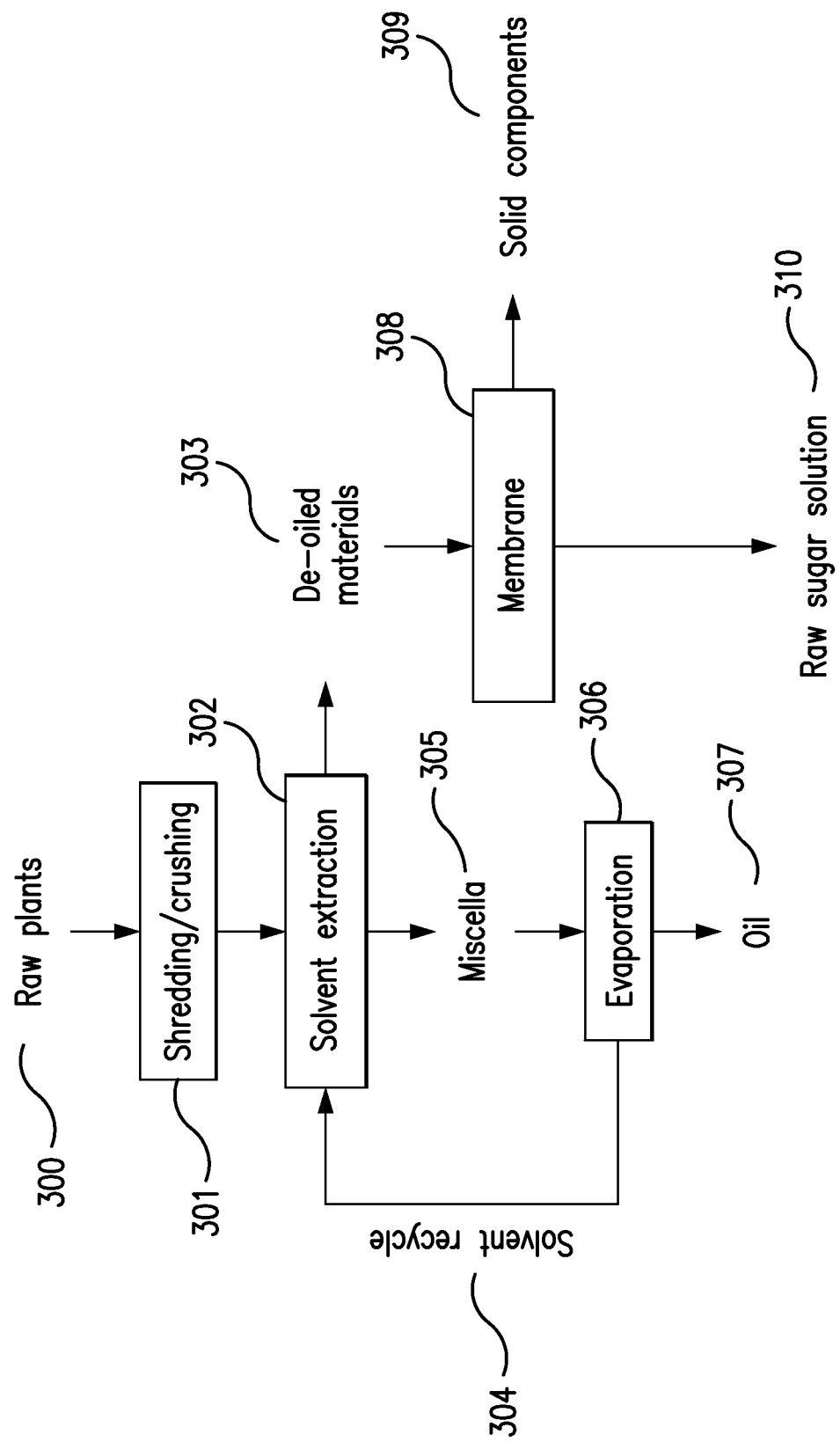
FIG. 3 illustrates a flow diagram of a separation process of oil and sugar by applying solvent extraction and membrane filtration.

Referring now to FIG. 3, it shows the process of the present disclosure where solvent extraction and membrane filtration are used to separate oil and sugars. In a first step, the raw plants 300 are mechanically treated in a shredding/crushing/pressing step 301 to release liquid containing oil and sugars from the stems and leaves of the plants. The mechanical treatment is as described with regard to mechanical treatment 101 in FIG. 1.

The mechanically treated mixture from the shredding/crushing/pressing step 301 is then routed to a solvent extraction step 302 where it is contacted with an organic solvent, such as hexane to separate the extracted oils as an oil/solvent miscella 305, from the sugars contained in the de-oiled materials stream 303. The organic solvent is contacted with the separated liquid stream for a period of time of about 10 to 120 min at a temperature of 68 to 150 DegF, and a pressure of about 101 kPa. The concentration of oil in the oil/solvent miscella 305 is from 0.1 wt % to more than 50 wt %. The recovery of oil from the mechanically treated mixture is from 0.5 wt % to 100 wt %, preferably from 5 wt % to 95 wt %. Raffinate from the solvent extraction process 302 is a de-oiled materials stream 303 containing the liquid sugars and solid components. The type of extraction equipment used is as described above. The concentration of liquid sugars in the de-oiled materials stream 303 is from 0.1 wt % to 60 wt %. The percent recovery of liquid sugars in the de-oiled materials stream 303 from the mechanically treated mixture ranges from 10 wt % to 100 wt %, preferably from 50 wt % to 99 wt %.

The separated oil/solvent miscella 305 is subjected to an evaporation step 306 to remove solvent from the oil so as to form an oil-rich stream 307 and a solvent recycle stream 304. The amount of solvent in the oil-rich stream 307 ranges from 0.01 wt % to 5 wt %. The organic solvent recovered from this step is recycled to the solvent extraction step 302 in a solvent recycle step 304.

The de-oiled materials stream 303 is then processed in a membrane filtration step to restrain suspended and precipitated solid components (retentate), in a solid components stream 309, while allowing sugars to pass through as a raw sugar solution stream 310. The recovery of raw sugar solution in stream 310 from the de-oiled materials stream ranges from 0.5 wt % to 100 wt %, preferably from 50 wt % to 99 wt %. Solid components other than raw sugar in the raw sugar solution stream 310 range from 0.1 wt % to 10 wt %. The percentage of solid components in the solid components stream 309 ranges from 10 wt % to 70 wt %. Since the suspended and precipitated solids have much larger size than the dissolved sugars, a membrane with a larger size may be used.

Figure 4:
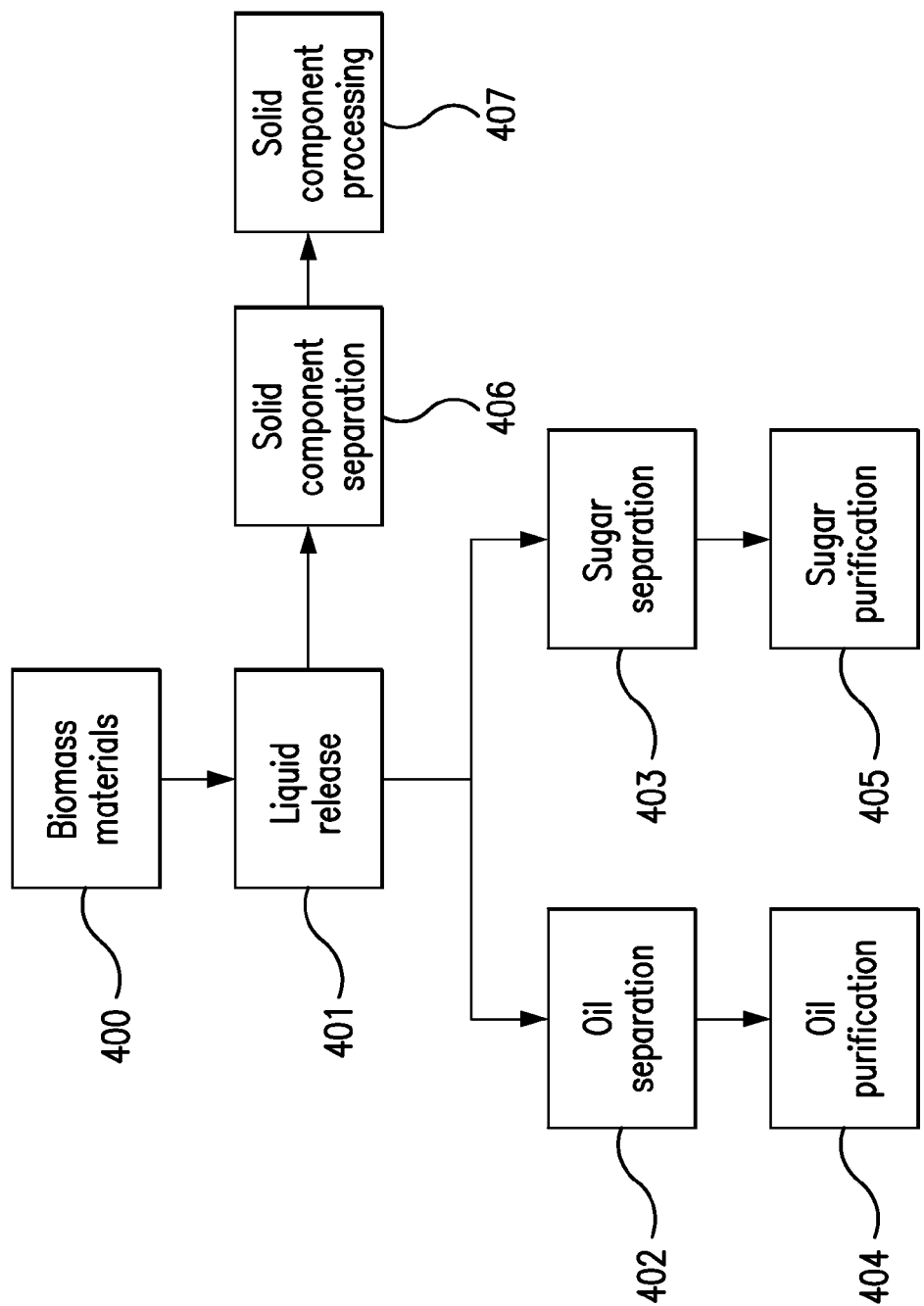
FIG. 4 is a schematic of the process steps of liquid release, oil separation and purification, sugar separation and purification, solid component separation and solid component processing.

Referring now to FIG. 4, in a first step, biomass 400 is mechanically treated in a liquid release step 401 to release liquid-containing oils and sugars from the biomass, resulting in a mechanically treated mixture containing the liquid-containing oils and sugars, and a solid component, where the mechanical treatment step includes at least one of a shredding, crushing or pressing step. The shredding, crushing and pressing steps are as described above. Such biomass includes any stems and leaves in plants that can accumulate more than 0.1 wt % of oils and sugars on a dry matter basis. Preferably, the stems and leaves in the plants have accumulated from 0.5 to 25 wt % of oil on a dry matter basis and from 1.0 to 55 wt % sugars on a dry matter basis. Oil is removed from the mechanically treated mixture in an oil separation step 402. The oil separation step 402 is selected from centrifugation, membrane filtration, or solvent extraction. The oil separation step 402 recovers from 0.5 wt % to 95 wt % of oils present in the mechanically treated mixture. Sugars are removed from the mechanically treated mixture in a sugar separation step 403. The sugar separation step 403 is selected from centrifugation or membrane filtration. The sugar separation step 403 collects from 0.5 wt % to 100 wt % of sugars present in the mechanically treated mixture. Following removal of oils and sugars, the mechanically treated mixture is subjected to a solid component separation step 406 to remove solid components from non-solids. The solid component separation step 406 removes from 80 wt % to 100 wt % of the solids present in the mechanically treated mixture. Solids recovered in the solid component separation step 406 are then forwarded to a solid component processing step 407. The equipment used in the solid component processing step 407 can include those normally used in physical, chemical or biological processes for solids, such as dryers to increase solids concentration, burners to burn the wet solids to produce thermal energy and other biological processing such as anaerobic digestion.

Sugars recovered in the sugar separation step 403 can be further purified in sugar purification step 405. Sugar purification step 405 can generally include the known physical, chemical or biological processes; for example, commercial processes, where the sugar solution can be treated with lime, heat and flocculants to neutralize acids and form a precipitate that adsorbs impurities and colorants. This treated sugar solution is then separated from the precipitate and subjected to a filtration step. The sugars in the filtered solution are treated with an evaporator to concentrate the sugars, and then in multiple-effect evaporators to produce a solids-containing syrup. The syrups are then treated in vacuum pans for crystallization. The sugar purification process also produces molasses as a byproduct. Oil purification step 404 can generally include the known physical, chemical or biological processes for oil; for example, commercial processes, where the oil can be treated with alkali's to neutralize free fatty acids, can be treated via a degumming step to remove phosphatides, be decolorized by treatment with clay or other adsorbents, and can be deodorized by vacuum distillation.

Figure 5:
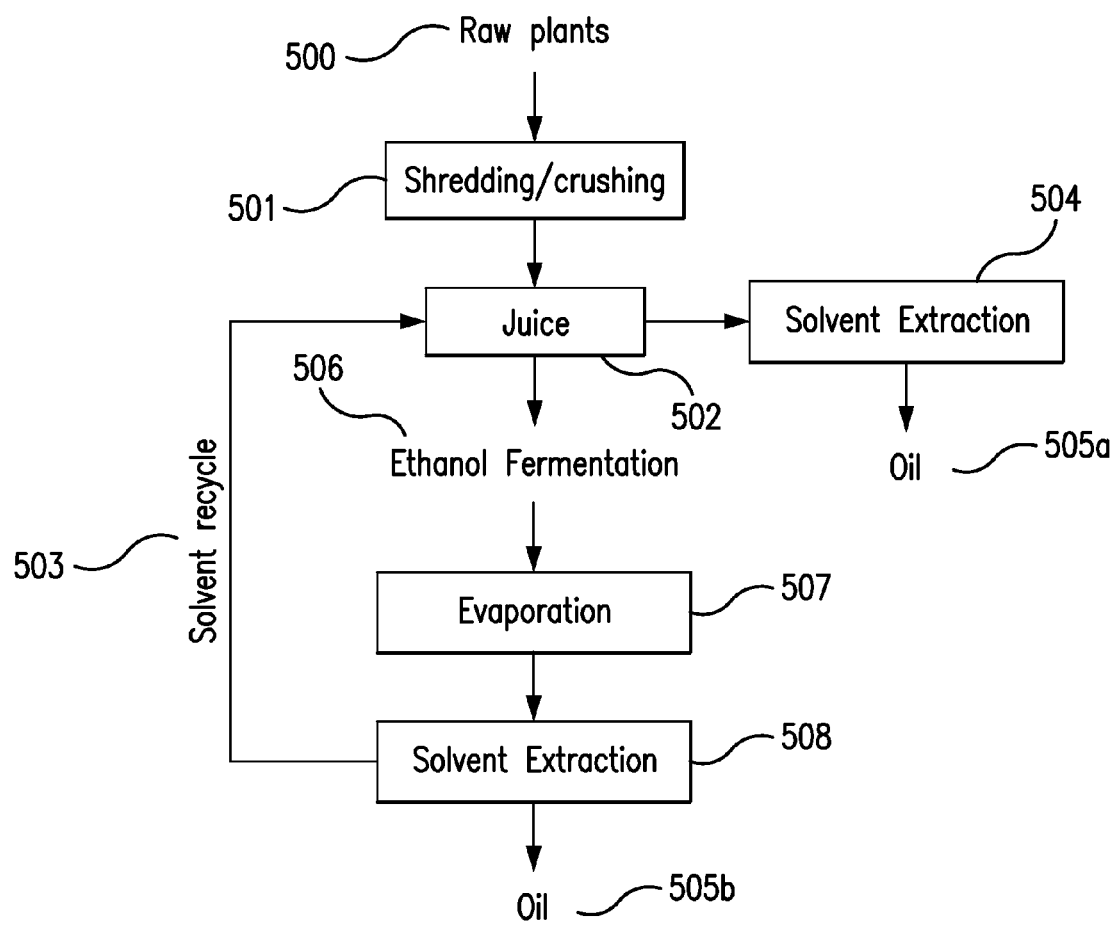
FIG. 5 illustrates a flow diagram of a separation process of oil and sugar by applying solvent extraction and ethanol fermentation.

Referring now to FIG. 5, in a first step, raw plants 500 are mechanically treated in a shredding/crushing/pressing step 501 to release liquid-containing oils and sugars from the raw plants, resulting in a mechanically treated mixture containing a juice stream 502 comprising the oil and sugars. The shredding, crushing and pressing steps are as described above. Also, as described above with respect to FIG. 3, the juice stream 502 may be processed in solvent extraction step 504 to produce oil stream 505*a*. However, the juice stream 502 may alternately be fermented in a fermentation step 506 to convert the sugars in the juice stream 502 to ethanol. Fermentation equipment that can be used includes any commercial equipment used for the fermentation of sugar-containing solutions. The formed ethanol is evaporated in an evaporation step 507 to a concentration below 0.01%, thereby forming a raw oil stream. The raw oil stream is extracted in a solvent extraction step 508 to separate an oil enriched stream 505*b*. Solvent can be returned to the juice stream 502 in a solvent recycle stream 503.

In the above-described processes for recovering oil and sugars from the stems and leaves of plants, the separation efficiency for the sugars is from 0.5 wt % to 99 wt %, preferably from 30 wt % to 96 wt %. The separation efficiency for oil is from 0.5 wt % to 95 wt %, preferably from 30 wt % to 90 wt %.

The following Examples further detail and explain the performance of the inventive oil/sugar separation processes. Those skilled in the art will recognize many variations that are within the spirit of the invention and scope of the claims.

EXAMPLE 1

A model biomass mixture was made by mixing 45 g of deionized water, 2.5 g of sugarcane bagasse (dry weight), 1.5 g of sucrose, and 1 g of corn oil. Bagasse was obtained from a sugarcane plant in Louisiana. Wet chemistry analysis showed that there was no sugar left in the bagasse samples. Corn oil was purchased from a local supermarket (Urbana, Ill.). Anhydrate sucrose powder and hexane solvent were purchased from the Fisher Scientific Inc. (Pittsburgh, Pa.).

In a process as shown in FIG. 1, the model mixture was centrifuged at 4,000 rpm for 3 min to remove the precipitated bagasse at room temperature. Supernatant, including oil and sucrose solution, was carefully moved to an empty bottle by pipette. The remaining bagasse was re-suspended with 45 g of DI water, followed by the second centrifugation at 4,000 rpm for 3 min. The supernatant from the first and second centrifugations was combined together. In the next step, the separated supernatant was subjected to an extraction step using hexane. The supernatant was added with 50 ml of hexane, followed by vortexing for 1 min, and incubating at 40° C. for 30 min. The oil/solvent phase was separated from the sucrose solution by the centrifugation method (1,000 rpm for 1 min). Next, the hexane solvent was separated from the oil by an evaporation process.

EXAMPLE 2

In a process as shown in FIG. 2, a model biomass mixture was prepared as in Example 1 and separated using a combination of centrifugal and membrane separation. The same steps were used to separate oil and sugar mixed liquid from bagasse as in Example 1. The collected supernatant was placed on a phase separation paper filter (1PS 9.0 cm, GE Healthcare Life Sciences, Little Chalfont, UK) under the vacuum condition. The un-dissolved oil was retained on the paper filter while dissolved sucrose passed through the paper filter. After filtration, 50 mL of DI water was added on the paper filter to wash the remaining sugar on the paper filter. The paper filter with retained oil was washed with 50 mL of hexane three times to ensure that all retained oil was dissolved in hexane. Next, the hexane solvent was separated from the oil by an evaporation process.

EXAMPLE 3

In a process as shown in FIG. 3, a model biomass mixture was prepared as in Example 1. 50 mL of hexane was added to the model biomass mixture at 40° C. for 30 min. After incubation, the sample was centrifuged at 4,000 rpm for 3 min. Supernatant, including oil/solvent phase and sugar solution, was transferred to an empty bottle by pipette. The extraction step was repeated twice. The de-oiled materials were then processed on a paper filter to restrain suspended and precipitated solid components (bagasse fibers) while allowing sucrose solution to pass through. The membrane filtration was repeated twice.

Two replicates were performed for each of the examples above. After each process, the recovered oil was determined gravimetrically. The recovered sucrose was determined by measuring the volume of the sucrose solution with a cylinder and the sucrose concentration with the YSI Sugar Analyzer (YSI Inc., Yellow Springs, Ohio). The separation efficiency of the examples was determined by the following equation:

$$\text{Separation efficiency} = \frac{\text{Mass of separated oil or sucrose}}{\text{Mass of added oil or sucrose}} \qquad (1)$$

Separation efficiencies were calculated for examples 1-3. These are summarized in Table 1.

TABLE 1

|  | Oil Separation efficiency | Sugar Separation efficiency |
| --- | --- | --- |
| Example 1 | 50.8 | 100.0 |
| Example 2 | 41.9 | 102.1 |
| Example 3 | 92.7 | 99.3 |

EXAMPLE 4

Lipid cane samples, treated by a biological/breeding technique and containing both oil and sugar in the stems and leaves, were processed using a juicer to extract juice by crushing and centrifugation. Oil was extracted from the juice using two strategies: first oil from the juice was solvent extracted with hexane. Second, oil was extracted by first fermenting the juice to ethanol. The rate of fermentation was very fast and all the juice fermented into ethanol in less than 24 hours. Ethanol was evaporated and residual material was solvent extracted with hexane for oil recovery. Lipid cane leaves were also ground to extract the oil. There was little or no oil in the pulp from lipid cane stems (after juice recovery).

The lipid cane samples, modified by a biological/breeding technique, had 0.83% oil present in the stems and 1.96% oil present in leaves. The stems were processed by the juicer, and oil from the stems was extracted directly from the juice to yield 0.1% of oil (separation efficiency of 12%.). When the same juice was first fermented, the ethanol evaporated, followed by extraction, 0.7% oil was recovered (separation efficiency of 84%). Similarly, the leaves of the lipid cane samples were processed in a juicer, with the juice then being fermented and the ethanol evaporated. When the remaining material was extracted with hexane, 1.35% oil was recovered (separation efficiency of 69%).

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Other features, advantages and embodiments of the invention disclosed herein will be readily apparent to those exercising ordinary skill after reading the foregoing disclosure. In this regard, while specific embodiments of the invention have been described in considerable detail, variations and modifications of these embodiments can be effected without departing from the spirit and scope of the invention as described and claimed.

We claim:

1. A method of recovering oil and sugars from a modified plant comprising stems and leaves, wherein the stems and leaves each contain oil selected from lipids, in an amount from 0.1 to 25 wt % on a dry matter basis and sugars selected from sucrose, glucose, fructose, other mono, di, or tri saccharides, or mixtures thereof in an amount from 0.1 to 55 wt % on a dry matter basis, the method comprising:
mechanically treating the plant to release liquid comprising the oil and sugars from the stems and leaves, thereby forming a mechanically treated mixture comprising the liquid and solid components, the mechanical treatment being selected from at least one of shredding, crushing and pressing;
separating the oil from the liquid, thereby forming an oil-rich stream, the oil separation step being selected from centrifugation, membrane filtration, or solvent extraction; and
separating the sugars from the liquid, thereby forming a sugar-rich solution, the sugar separation step being selected from centrifugation or membrane filtration.

2. The method of claim 1, further comprising purifying the oil-rich stream, the oil purification step being selected from physical, chemical or biological processes.

3. The method of claim 1, further comprising purifying the sugar-rich solution, the sugar-solution purification step being selected from physical, chemical or biological processes.

4. The method of claim 1, further comprising treating the solid component in a solid component processing step selected from physical, chemical or biological processes.

5. The method of claim 1 wherein the plant is a grass.

6. The method of claim 5 wherein the grass is a saccharinae.

7. The method of claim 6 wherein the saccharinae is sugarcane or sweet sorghum.

8. The method of claim 1 wherein the mechanical treatment comprises crushing in a roller mill.

9. The method of claim 8 wherein during crushing, the mechanically treated mixture is immersed in hot water or solvents.

10. The method of claim 1 wherein the lipids are selected from fats, waxes, sterols, monoglycerides, diglycerides, triglycerides, phospholipids or mixtures thereof.

11. The method of claim 1 wherein the mechanical treatment step comprises at least two of shredding, crushing and pressing.

12. The method of claim 1 wherein the mechanical treatment step comprises shredding, crushing and pressing.

13. The method of claim 1 wherein the sugars are selected from sucrose, other di, or tri saccharides, or mixtures thereof.

14. The method of claim 1 wherein the lipids are present in an amount from 0.5 to 25 wt %.

15. The method of claim 1 wherein the sugars are present in an amount from 1.0 to 55 wt %.

16. The method of claim 1 wherein the lipids are present in an amount from 0.5 to 25 wt % and the sugars are present in an amount from 1.0 to 55 wt %.

17. A method of recovering oil and sugars from a modified plant comprising stems and leaves, wherein the stems and leaves each contain oil selected from lipids in an amount from 0.1 to 25 wt % on a dry matter basis and sugars selected from sucrose, glucose, fructose, other mono, di, or tri saccharides, or mixtures thereof in an amount from 0.1 to 55 wt % on a dry matter basis, the method comprising:
mechanically treating the plant to release liquid comprising oil and sugars from the stems and leaves, thereby forming a mechanically treated mixture comprising the liquid and solid components, the mechanical treatment being selected from at least one of shredding and crushing;
separating the liquid from the solid component in a liquid-solid separation step selected from centrifugation or filtration, thereby forming a separated liquid stream and a separated solid component stream;
separating the oils from the sugars in the separated liquid stream in a solvent extraction step, thereby forming a raw sugar solution stream and a miscella stream comprising oil and solvent;
removing solvent from the miscella stream in an evaporation step, thereby forming an oil-rich stream and a solvent recycle stream; and
returning the solvent stream to the solvent extraction step.

18. A method of recovering oil and sugars from a modified plant comprising stems and leaves, wherein the stems and leaves each contain oil selected from lipids in an amount from 0.1 to 25 wt % on a dry matter basis and sugars selected from sucrose, glucose, fructose, other mono, di, or tri saccharides, or mixtures thereof in an amount from 0.1 to 55 wt % on a dry matter basis, the method comprising:

mechanically treating the plant to release liquid comprising oil and sugars from the stems and leaves, thereby forming a mechanically treated mixture comprising the liquid and solid components, the mechanical treatment being selected from at least one of shredding and crushing;

separating the liquid from the solid component in a liquid-solid separation step selected from centrifugation or filtration, thereby forming a separated liquid stream and a separated solid component stream;

separating the oil from the sugars in the separated liquid stream in a membrane filtration step, thereby forming a raw sugar solution stream and an oil-rich stream comprising oil; and concentrating the oil in the oil-rich stream in an evaporation step, thereby forming a concentrated oil stream.

19. A method of recovering oil and sugars from a modified plant comprising stems and leaves, wherein the stems and leaves each contain oil selected from lipids in an amount from 0.1 to 25 wt % on a dry matter basis and sugars selected from sucrose, glucose, fructose, other mono, di, or tri saccharides, or mixtures thereof in an amount from 0.1 to 55 wt% on a dry matter basis, the method comprising:

mechanically treating the plant to release liquid comprising oil and sugars from the stems and leaves, thereby forming a mechanically treated mixture comprising the liquid and solid components, the mechanical treatment being selected from at least one of shredding and crushing;

extracting the mechanically treated mixture in a solvent extraction step, thereby forming a de-oiled material stream comprising sugars and a solid component, and a miscella stream comprising oil and solvent;

removing solvent from the miscella stream in an evaporation step, thereby forming an oil-rich stream and a solvent recycle stream; and separating the sugars from the solid component in the de-oiled material stream in a membrane filtration step, thereby forming a raw sugar solution and a solid component stream.

20. A method of recovering oil and sugars from a modified plant comprising stems and leaves, wherein the stems and leaves each contain oil selected from lipids in an amount from 0.1 to 25 wt % on a dry basis and sugars selected from sucrose, glucose, fructose, other mono, di, or tri saccharides, or mixtures thereof in an amount from 0.1 to 55 wt % on a dry matter basis, the method comprising:

mechanically treating the plant to release liquid from the stems and leaves, thereby forming a mechanically treated mixture comprising a juice stream comprising the oil and sugars, the mechanical treatment being selected from at least one of shredding and crushing;

fermenting the juice stream in a fermentation step to convert the sugars to ethanol, thereby forming a fermented mixture;

evaporating the ethanol from the fermented mixture in an evaporation step, thereby forming a raw oil stream; and extracting the raw oil stream in a solvent extraction step to separate oil from the raw oil stream, thereby forming an oil enriched stream.

* * * * *